US012765928B2

(12) United States Patent
Maxwell et al.

(10) Patent No.: US 12,765,928 B2
(45) Date of Patent: Oct. 20, 2026

(54) BONE SCREW FIXATION SYSTEM

(71) Applicants: Keith Melvin Maxwell, Hendersonville, NC (US); David Wiles, Chattanooga, TN (US); Julian Price, Bogart, GA (US); Justin Splane, Knoxville, TN (US); Alicia Henderson, Knoxville, TN (US); Jayden Garfield, Knoxville, TN (US); Matthew B. Kubo, Knoxville, TN (US)

(72) Inventors: Keith Melvin Maxwell, Hendersonville, NC (US); David Wiles, Chattanooga, TN (US); Julian Price, Bogart, GA (US); Justin Splane, Knoxville, TN (US); Alicia Henderson, Knoxville, TN (US); Jayden Garfield, Knoxville, TN (US); Matthew B. Kubo, Knoxville, TN (US)

(73) Assignee: Choice Spine, LLC, Knoxville, TN (US)

(*) Notice: Subject to any disclaimer, the term of this patent is extended or adjusted under 35 U.S.C. 154(b) by 564 days.

(21) Appl. No.: 17/867,034

(22) Filed: Jul. 18, 2022

(65) Prior Publication Data

US 2023/0032203 A1 Feb. 2, 2023

Related U.S. Application Data

(63) Continuation-in-part of application No. 17/866,798, filed on Jul. 18, 2022, now Pat. No. 12,011,201.

(Continued)

(51) Int. Cl.

| | |
|---|---|
| ***A61B 17/86*** | (2006.01) |
| ***A61B 17/17*** | (2006.01) |
| ***A61F 2/30*** | (2006.01) |

(52) U.S. Cl.

CPC ...... *A61B 17/8605* (2013.01); *A61B 17/1717* (2013.01); *A61B 17/869* (2013.01); *A61F 2/3094* (2013.01); *A61F 2002/30985* (2013.01)

(58) Field of Classification Search

CPC ........ A61B 17/84–8695; A61B 17/8875–8888

See application file for complete search history.

(56) References Cited

U.S. PATENT DOCUMENTS 5,735,898 A * 4/1998 Brånemark ......... A61F 2/30749 606/317

6,022,352 A * 2/2000 Vandewalle ......... A61B 17/746 606/65

(Continued)

OTHER PUBLICATIONS

International Searching Authority, Patent Cooperation Treaty, Notification of Transmittal of the International Search Report and the Written Opinion of the International Searching Authority, or the Declaration (PCT Rule 44.1), PCT/US22/37563, ISA/US Alexandria, Virginia, USA, Kari Rodriquez, date of mailing Oct. 25, 2022.

*Primary Examiner* — Eduardo C Robert

*Assistant Examiner* — Steven J Cotroneo

(74) *Attorney, Agent, or Firm* — Luedeka Neely, P.C.

(57) ABSTRACT

A bone screw fixation system includes a bone screw body having a screw head at one end of the screw and a screw tip at an opposite end of the screw, the screw head having an internal complex geometric shaped drive and internal threads within the screw head; and a screw inserter compatible with the screw head and having a complex geometric shaped drive configured to matingly engage the internal complex geometric shaped drive of the screw head and a threaded tip configured to thread into the internal threads of the screw head.

2 Claims, 22 Drawing Sheets

Related U.S. Application Data

(60) Provisional application No. 63/224,017, filed on Jul. 21, 2021.

(56) References Cited

U.S. PATENT DOCUMENTS

| | | | | |
|---|---|---|---|---|
| 9,387,025 | B2 * | 7/2016 | Santangelo | A61B 17/864 |
| 10,179,014 | B1 * | 1/2019 | Menmuir | A61B 17/869 |
| 10,631,905 | B2 * | 4/2020 | Asfora | A61B 17/8625 |
| 2004/0015172 | A1 * | 1/2004 | Biedermann | A61B 17/869<br>606/328 |
| 2006/0235338 | A1 * | 10/2006 | Pacheco | A61B 5/1076<br>600/587 |
| 2006/0241623 | A1 * | 10/2006 | Lim | A61B 17/8625<br>606/265 |
| 2007/0043379 | A1 * | 2/2007 | Sullivan, Jr. | A61B 17/8615<br>606/104 |
| 2008/0065070 | A1 * | 3/2008 | Freid | A61B 17/1757<br>606/279 |
| 2012/0053627 | A1 * | 3/2012 | Sojka | A61B 17/0485<br>606/232 |
| 2015/0272646 | A1 * | 10/2015 | Russell | A61B 17/8811<br>606/93 |
| 2016/0220291 | A1 * | 8/2016 | Russell | A61B 17/8811 |
| 2019/0343565 | A1 * | 11/2019 | Tempco | A61B 17/863 |
| 2020/0107868 | A1 | 4/2020 | Kolb | |
| 2020/0163704 | A1 | 5/2020 | Shmueli | |
| 2020/0289171 | A1 * | 9/2020 | Hoos | A61B 17/7092 |
| 2021/0153911 | A1 * | 5/2021 | Stuart | A61B 17/7098 |

* cited by examiner

BONE SCREW FIXATION SYSTEM

FIELD

The present disclosure relates to fixation systems for bones. More particularly, the disclosure relates to a fixation system having bone screws of improved manufacture, structure and aesthetics, and to a system configured for installation of the bone screws and methods for installation of bone screws.

BACKGROUND

Improvement is desired in the provision of bone fixation systems. In particular, improvement is desired for bone fixation systems for the sacroiliac (SI) joint. The SI joint is located in the pelvis and links the iliac bone (pelvis) to the sacrum (lowest part of the spine above the tailbone).

SUMMARY

The disclosure relates to a bone screw fixation system and to methods for installation of bones screws.

In one aspect, a bone screw fixation system according to the disclosure includes a bone screw body having a screw head at one end of the screw and a screw tip at an opposite end of the screw, the screw head having an internal complex geometric shaped drive and internal threads within the screw head. The system also includes a screw inserter compatible with the screw head and having a complex geometric shaped drive configured to matingly engage the internal complex geometric shaped drive of the screw head and a threaded tip configured to thread into the internal threads of the screw head.

In another aspect, a bone screw fixation system according to the disclosure includes a pin configured to have a distal end installable into a bone; a tissue dilator placeable over the pin with a distal end of the dilator proximate the distal end of the pin such that the pin extends past a proximal end of the tissue dilator; a depth gauge having depth markings thereon, the depth gauge being positionable onto the proximal end of the dilator. A proximal end of the pin substantially aligns with one of the depth markings to designate a length dimension; and a bone screw installable into the bone.

The bone screw has a body having a screw head at one end of the screw, a screw tip at an opposite end of the screw, and a cannula extending from the screw head to the screw tip. The bone screw has a length and the length of the bone screw is selected to correspond to the length dimension designated by the depth marking of the depth gauge that the proximal end of the pin is substantially aligned with.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIGS. 20A-40B depict use of the fixation system and methodologies for installation of bone screws according to the disclosure.

DETAILED DESCRIPTION

Figure 1:
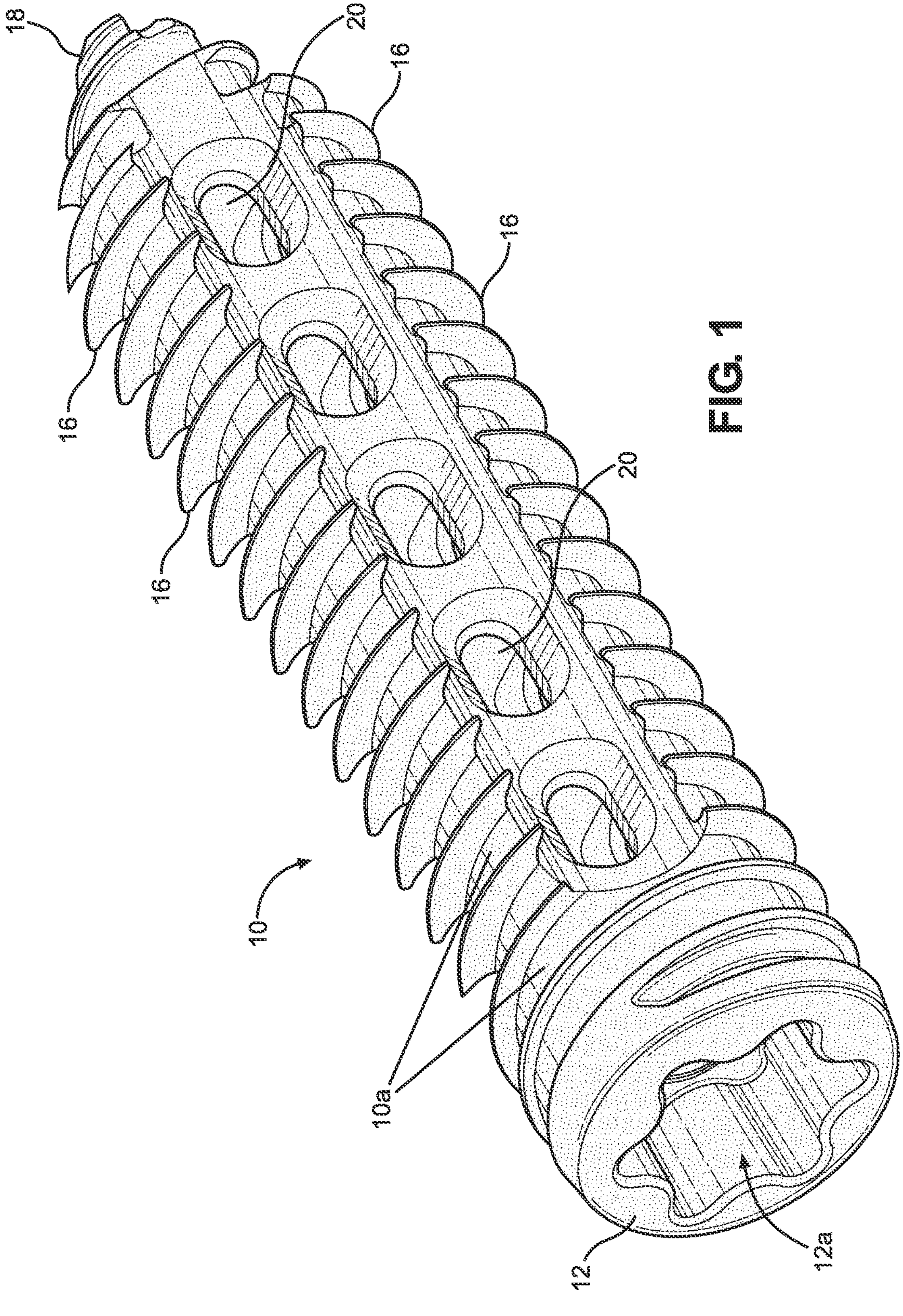
FIG. 1 is a perspective view of a bone screw according to the disclosure.
Figure 2:
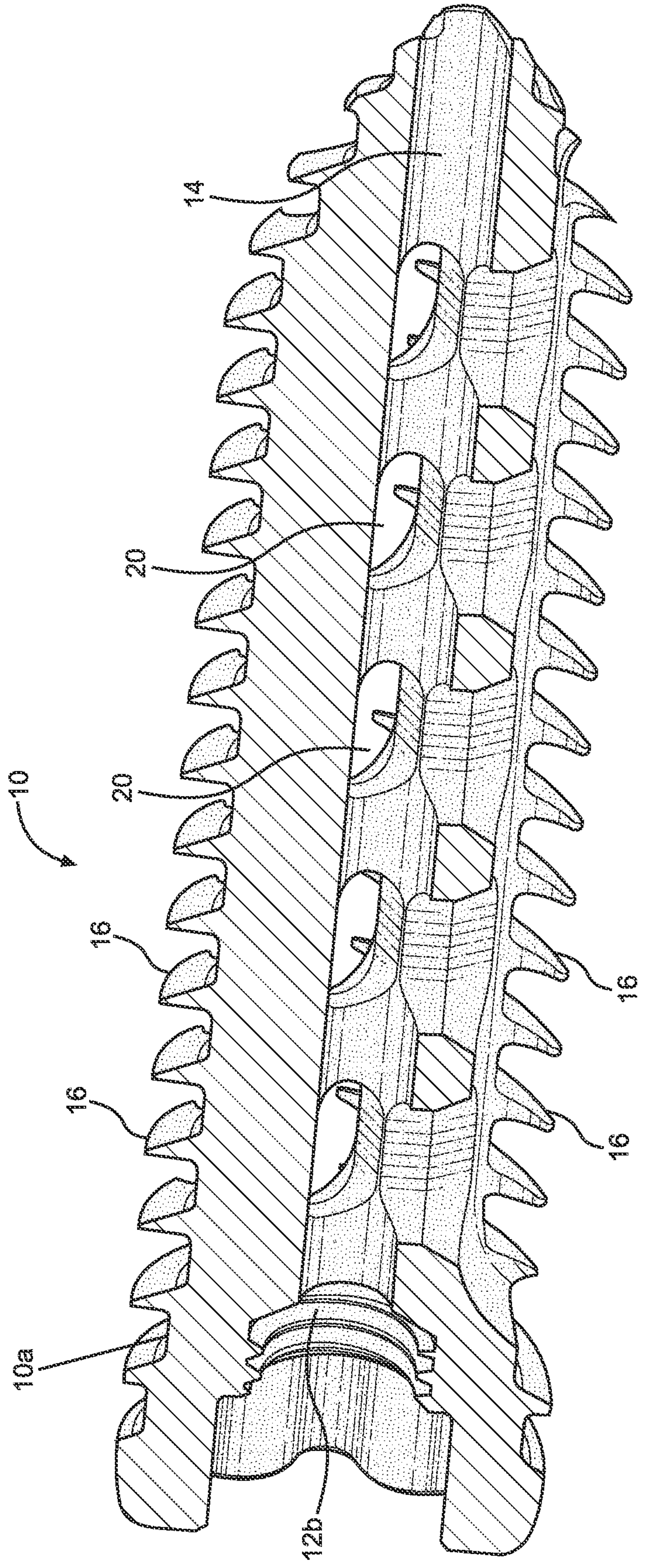
FIG. 2 is a cross-sectional view thereof.
Figure 3:
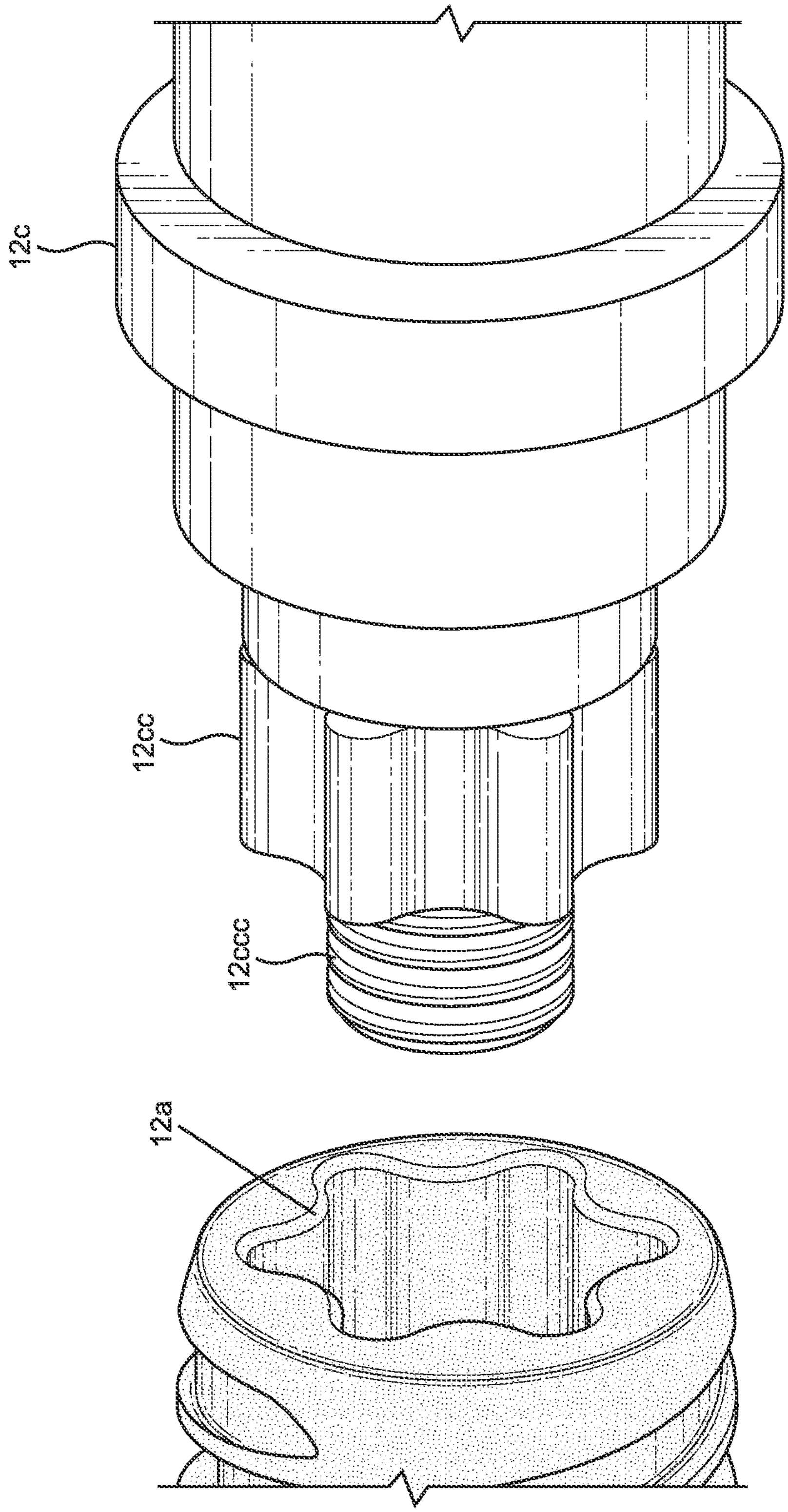
FIG. 3 shows a head of the screw and a drive configured to drive the screw.
Figure 4:
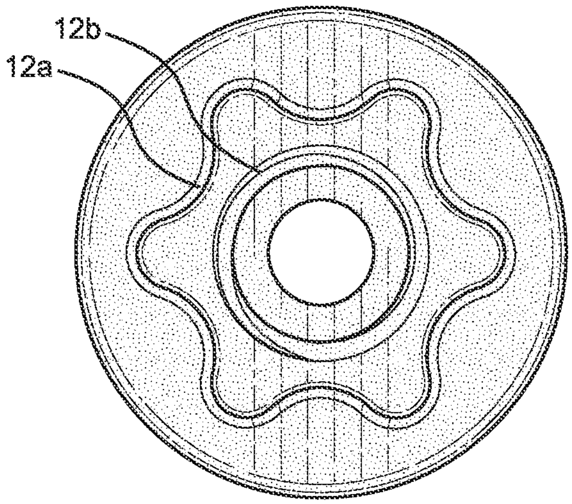
FIG. 4 is the head end view of the bone screw.
Figure 5:
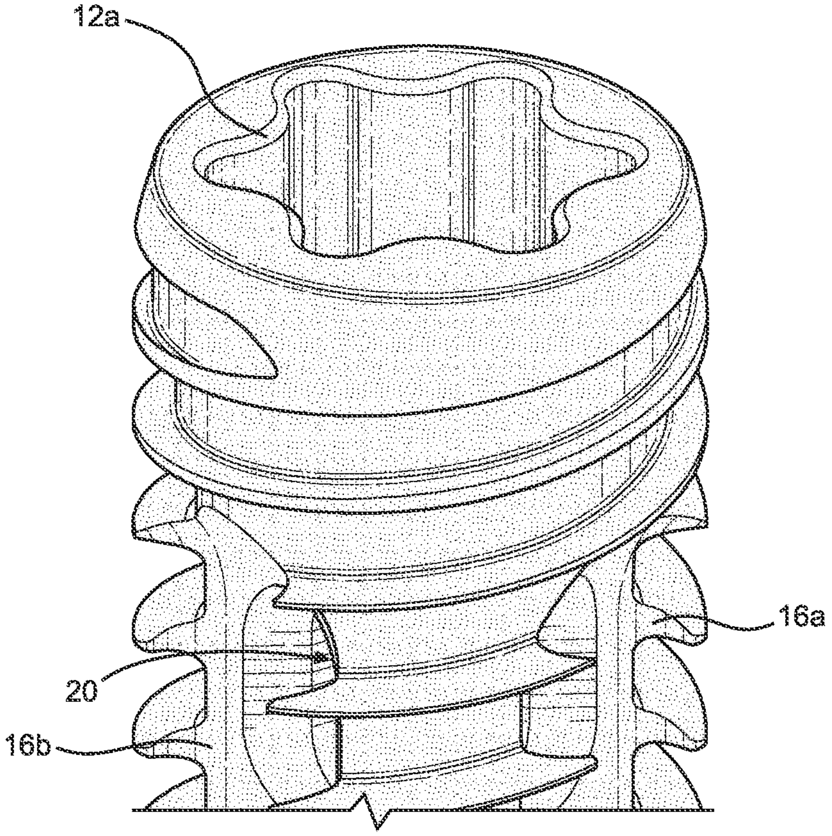
FIG. 5 is a closeup perspective view of a head of the bone screw.
Figure 6:
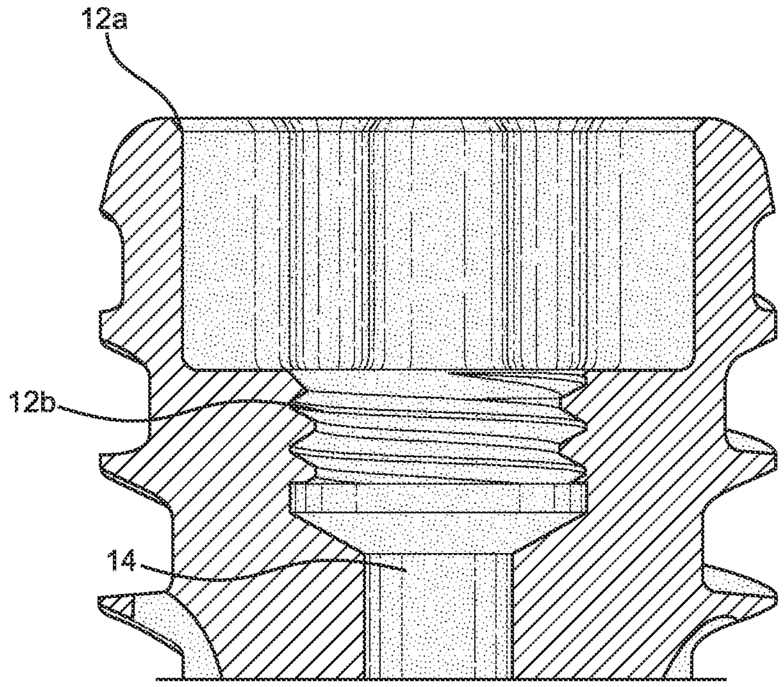
FIG. 6 is a cross-sectional view of the head.
Figure 7:
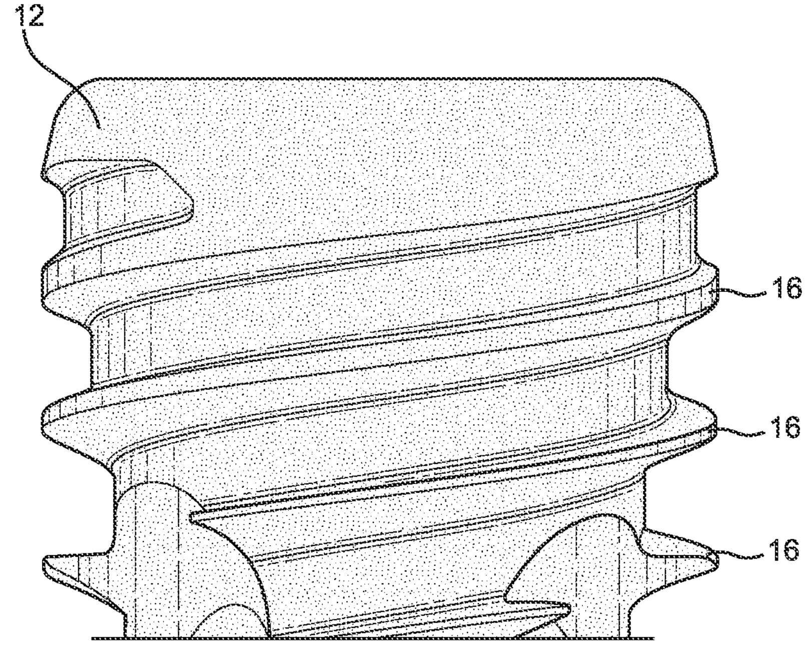
FIG. 7 is a closeup view of the side of the head.
Figure 8:
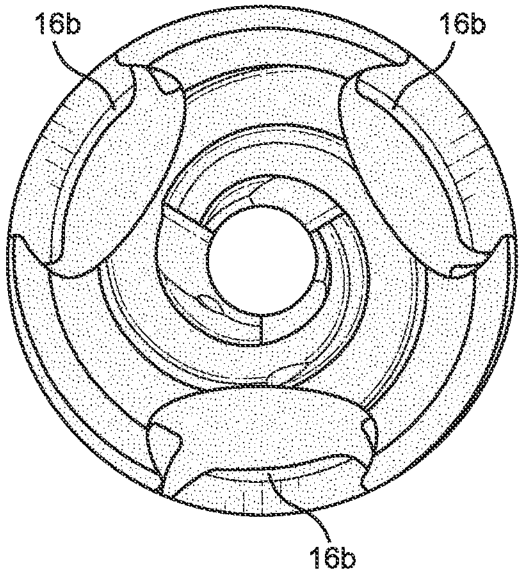
FIG. 8 is a tip end view of the bone screw.

With reference to the drawings, there is shown components and methods associated with a bone fixation system according to the disclosure. The system includes a variety of components discussed in detail below, including an implant in the form of a bone screw of improved construction and aesthetics. The system also includes specially configured instruments as described herein along with various conventional surgical instruments such as those discussed herein including a driver, a pin puller, tap/drill and pin holder.

In broad overview, the bone fixation system of the disclosure is used to install one or more of the bone screws. In the described embodiment, the system is shown and discussed in connection with installation of a bone screw at the sacroiliac joint of a patient, although it will be understood that the system may be used for installation of implants at various locations within the body of a patient.

The procedure for installation has various aspects, but generally the procedure may involve use of a fluoroscope for location of the site for installation of the pin. Initially, a pin is forcefully inserted or driven into the bone at a desired location and angle. Following this, tissue is retracted using the first dilator, the second dilator, and the third dilator, although the third dilator is not always used. Next, the internal dilators are removed and the site is prepared for the bone screw using a tap, awl, and/or drill guided over the pin through the last dilator. The bone screw is then loaded onto an inserter and guided over the pin into the screw hole. The instruments are removed and the procedure repeated for each additional bone screw needed for the surgery.

Initially, an implant in the form of a bone screw is described in connection with FIGS. 1-14. Following this, components of a fixation system for installation of the bone screw is described in connection with FIGS. 15A-19. Use of the system and methodologies for installation of the bone screw are described in connection with FIGS. 20A-40B. Finally, packing of a thus installed bone screw with a bone graft material is depicted in FIGS. 41A-42C.

FIGS. 1-14

With reference to FIGS. 1-14, there is shown a bone screw 10 of improved construction and aesthetics according to the disclosure. The bone screw 10 is particularly configured for promoting bone growth to and through the screw. The bone screw 10 is particularly suitable for installation at the sacroiliac joint of a patient but may be used for other sites of the body.

The bone screw 10 is preferably manufactured by 3-D printing and is most preferably printed using 3-D printing techniques know as Direct Metal Laser Sintering (DMLS)

techniques using Titanium Alloy (Ti-6Al-4V). One significant advantage of manufacture of the bone screw 10 by DMLS is that the bone screw 10 may be used in surgeries as printed and requires no post-printing machining. This enables reduced manufacturing costs and enables more consistent quality with reduced labor requirements.

Manufacture of the bone screw 10 by DMLS techniques also advantageously enables unique structures, shapes, and other features to be provided on the bone screw 10. For example, the screw 10 has a bone receptive rugous outer surface and has porous structures on the surface of the screw 10 and internal features of the screw 10 as described herein.

Manufacture of the screw 10 by DMLS has been observed to provide the bone screw 10 with a roughened surface which is believed to be advantageous for promoting bone growth. For example, as shown in FIG. 1, the screw 10 as formed by DMLS has a body 10*a* with an exterior roughened surface over the entirety of the screw that is configured to be more receptive to bone growth onto the surface than the surface of conventional titanium screws that have a relatively smooth surface.

The manufacturing method also facilitates formation of a head 12 of the screw 10 that facilitate interaction of the bone screw 10 with insertion tools. As shown, the head 12 is configured to include insertion features such as a large internal or recessed complex geometric shaped drive 12*a*, such as a T-50 drive or hexalobe-shaped drive, and internal threads 12*b* within the head 12 and below the drive 12*a*. In this manner, a compatibly configured screw inserter 12*c* such as shown having a T-50 drive 12*cc* and threaded tip 12*ccc* may be utilized for more secure connection between the inserter and the bone screw 10. The drive 12*cc* fits the drive 12*a* and the threaded tip 12*ccc* threads into the internal threads 12*b*. The bone screw 10 is also formed to include a cannula 14 for receiving a guide wire if desired.

The screw 10 has a triangular cross-section and is formed to include threads 16 configured for screwing into a bone. An upper portion of the threads 16 continue their runout onto the head 12 for aiding in installation of the screw 10 and in providing a tactile feel to the physician when seating the screw 10. Also, the threads 16 blunt towards the head 12 to help prevent soft tissue damage if the head 12 of the screw 10 is left proud.

Another feature of the bone screw 10 enabled by the manufacturing method is the provision of overhanging thread portions 16*a*. For example, as shown, the threads 16 are continuous around the body 10*a* at the head 12 and a tip 18. However, in between the head 12 and the tip 18 the threads 16 are not continuous and have exposed ends which provide the overhanging thread portions 16*a*.

As seen, the overhanging thread portions 16*a* are spaced apart, with unthreaded channels 16*b* between the sets of overhanging thread portions 16*a*. The overhanging thread portions 16*a* as shown are provided in three radially spaced apart sets but may be in other spacings. The overhanging thread portions 16*a* extend above or overhanging a portion of the unthreaded channels 16*b*. The combination of the overhanging thread portions 16*a* and the unthreaded channels 16*b* provides three fluted channels that are configured for improvement of bone collection onto the screw 10 during installation and subsequent growth of bone to and through the screw 10.

Figure 9:
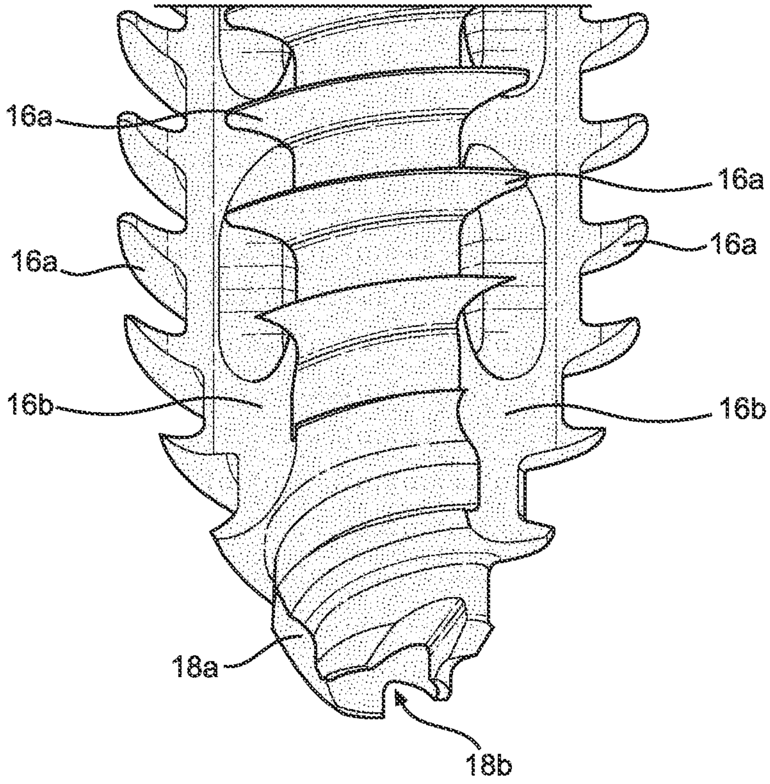
FIG. 9 is a closeup side view of the tip of the bone screw.
Figure 10:
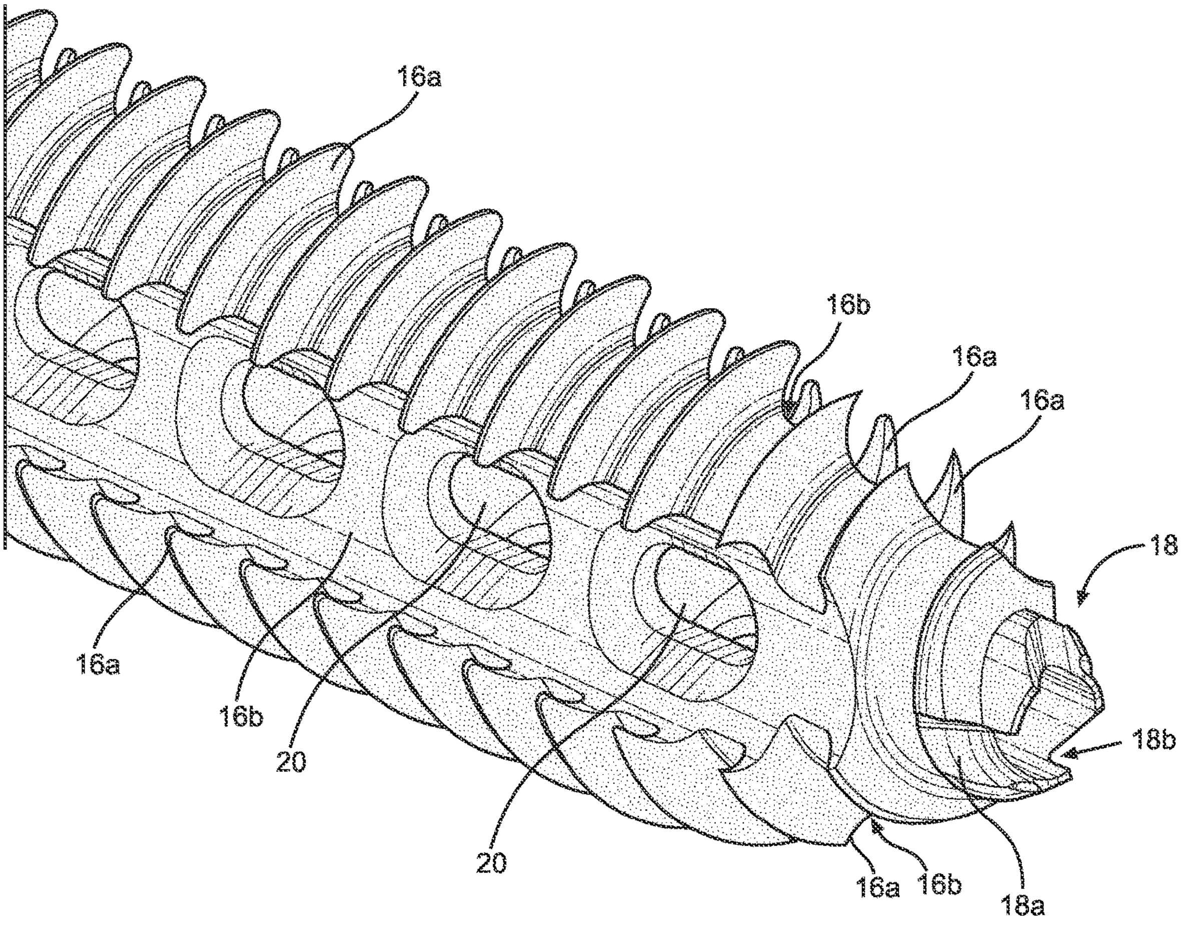
FIG. 10 is a closeup perspective view of the tip of the bone screw.

The tip 18 is configured as a cutting tip with cutting flutes 18*a* defining cutouts 18*b* (FIG. 9). During installation of the screw 10 into the bone, as bone is cut the channels 16*b* fill with cut bone, which aids in fusion of the bone to the screw 10 as the bone heals.

Another feature of the screw 10 is the provision of openings or windows 20 along the length of the bone screw 10 and located in the unthreaded channels 16*b* between the sets of overhanging thread portions 16*a*. The windows 20 provide access for bone to feed into interior portions of the screw 10 and provide zones of continuous porosity and permeability. The windows 20 are provided to facilitate the growth of bone through the screw 10 and along the surfaces of the screw 10.

Each of the windows 20 of one of the unthreaded channels 16*b* is preferably aligned with correspondingly located windows 20 of the other unthreaded channels 16*b*. As depicted, the windows 20 are desirably oblong in shape to provide open areas while retaining strength if the screw 10. However, the windows 20 may be of other shape. The windows 20 may be of uniform or non-uniform dimension. The dimensions of the windows 20 desirably correspond to and change to correspond to changes in the diameter and length of the screw 10 to preserve the structural strength of the screw 10 while still maximizing the surface area of the windows 20 for promoting bone growth to and through the screw 10.

Figure 12:
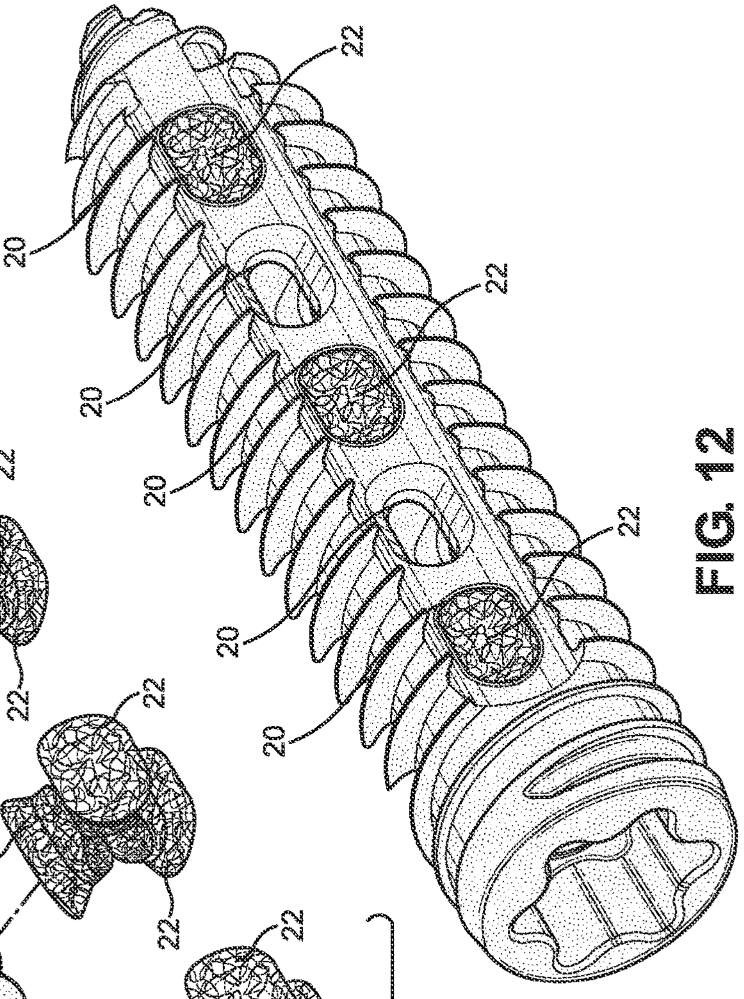
FIGS. 11-14 show window features of the bone screw.
Figure 11:
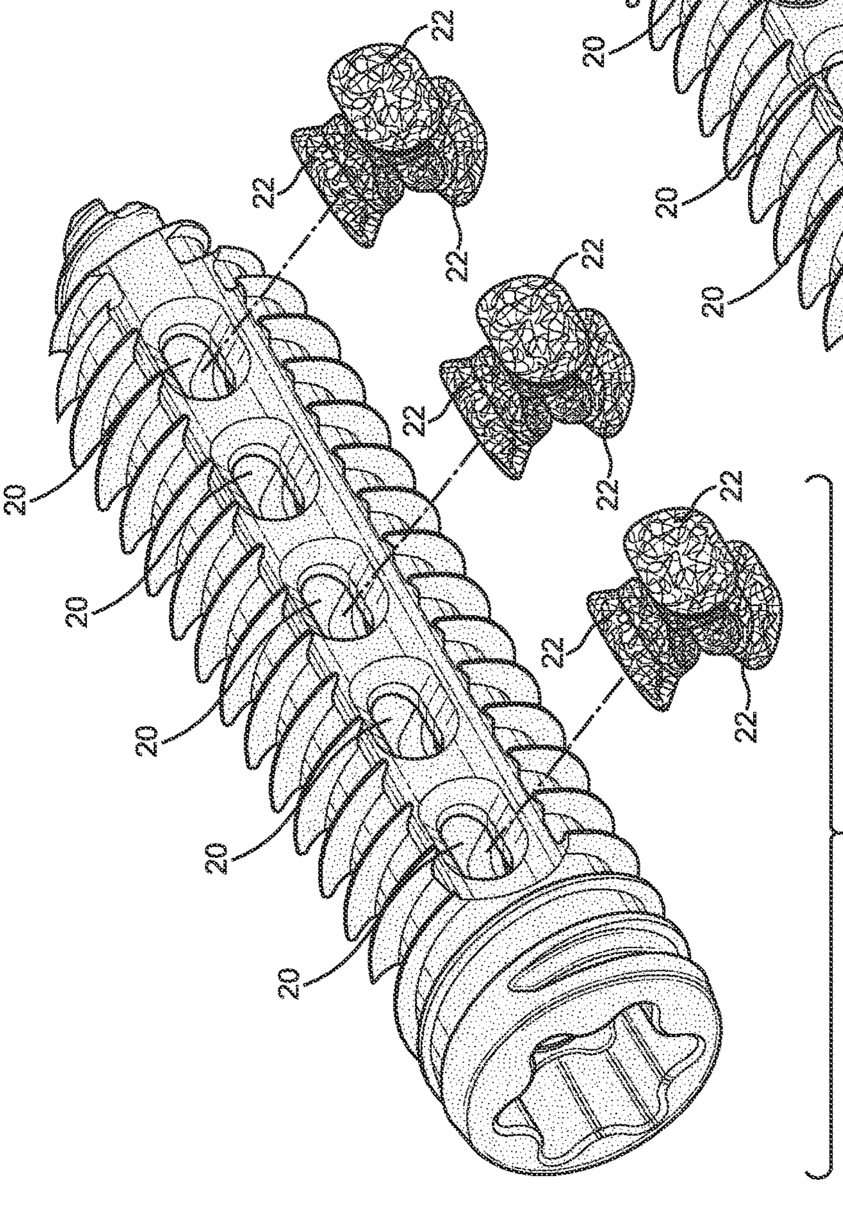
Figure 13:
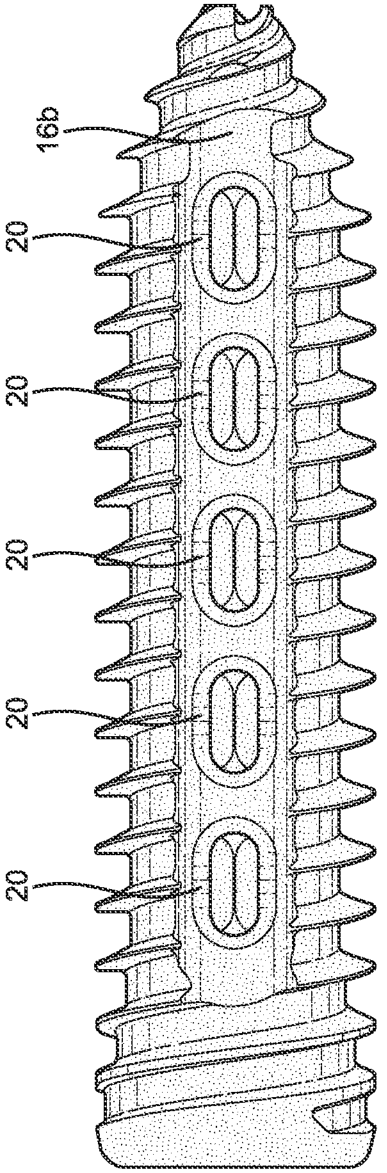
Figure 14:
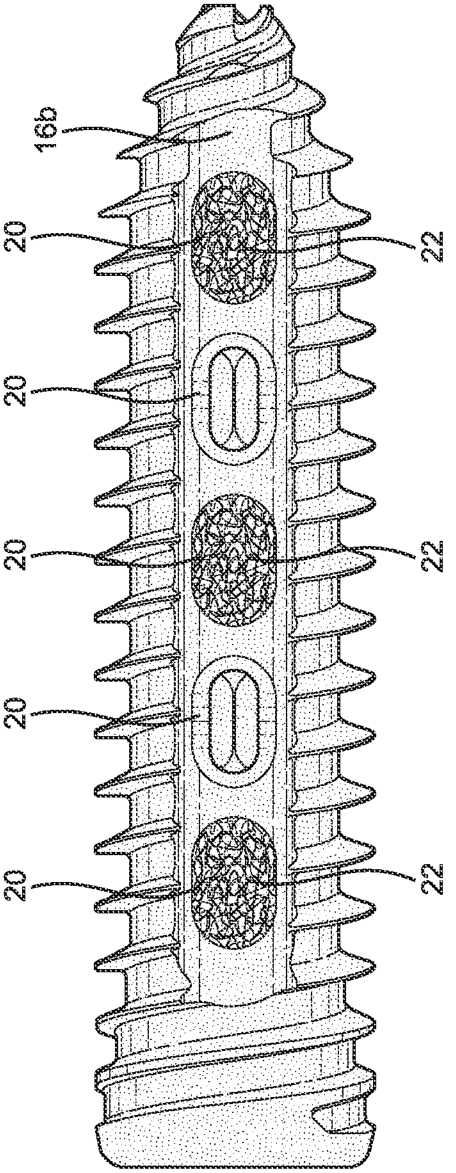

One or more of the windows 20 may be formed to include a permeable and porous fill 22 occupying the window 20. The fill 22 is formed during the printing of the screw 10 by DMLS and is integrally formed as part of the structure of the window as it is printed as shown in FIG. 12. As shown, the screw 10 may be formed with all of the windows 20 open, or a combination of some of the windows 20 open and some having the fill 22, or even all having the fill 22.

The bone screw 10 may be provided in various dimensions and without the windows. It will be appreciated that the rough surface of the DMLS printed screw in of itself provides a surface that is favorable to promote bone growth to the screw. However, the use of the windows 20 as described is preferred.

FIGS. 15A-19

Figure 15A:
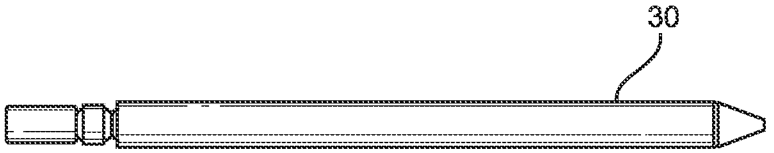
FIGS. 15A-19 show components of a fixation system for installation of the bone screws.
Figure 15B:
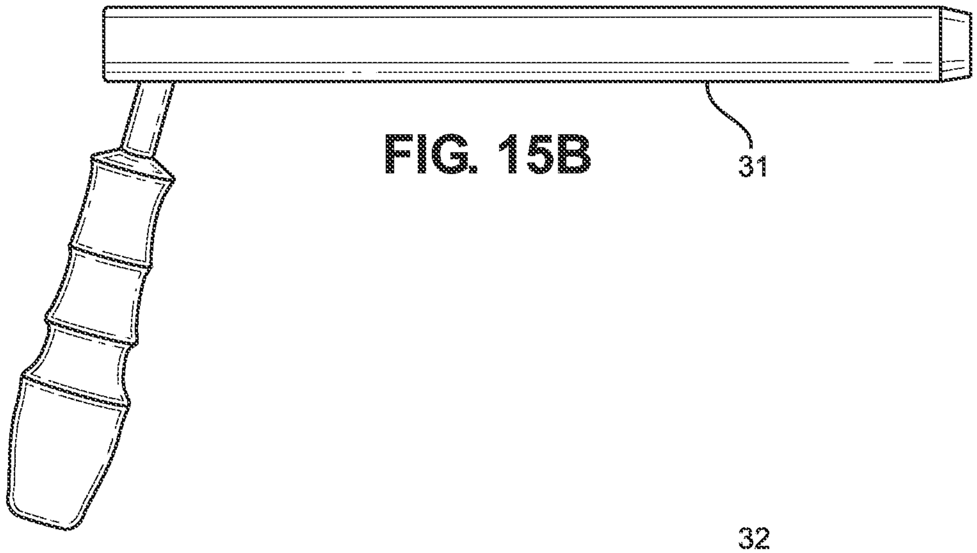
Figure 15C:
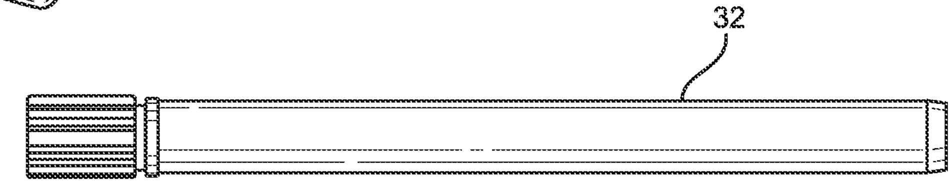
Figure 15D:
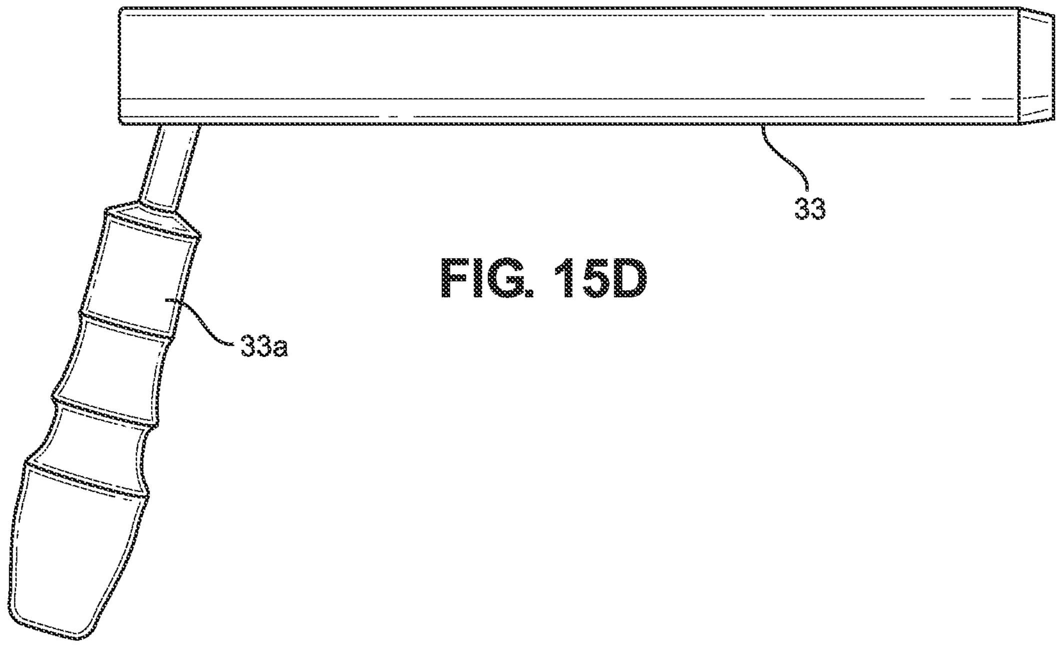

Components of a fixation system for installation of the bone screw 10 according to the disclosure are described in connection with FIGS. 15A-19. FIG. 15A shows a first tissue dilator 30, FIG. 15B shows a second handled tissue dilator 31, FIG. 15C shows a second tissue dilator 32, and FIG. 15D shows a third handled tissue dilator 33.

As will be noted, the first tissue dilator 30 and the second tissue dilator 32 do not have handles. The second handled tissue dilator 31 and the third handled tissue dilator 33 have handles 31*a* and 33*a*, respectively. The first tissue dilator 30 has the smallest diameter. The second handled tissue dilator 31 and the second tissue dilator 32 each have the same diameter, which is larger than the diameter of the first tissue dilator 30. The third handled tissue dilator 33 has a larger diameter than that of the second handled tissue dilator 31 and the second tissue dilator 32.

Figure 16:
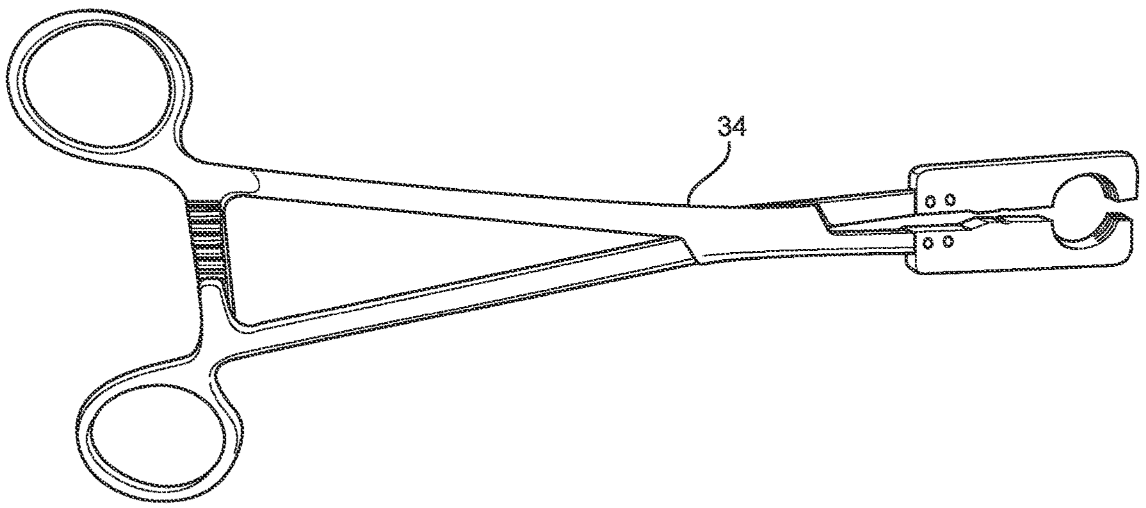
Figure 17A:
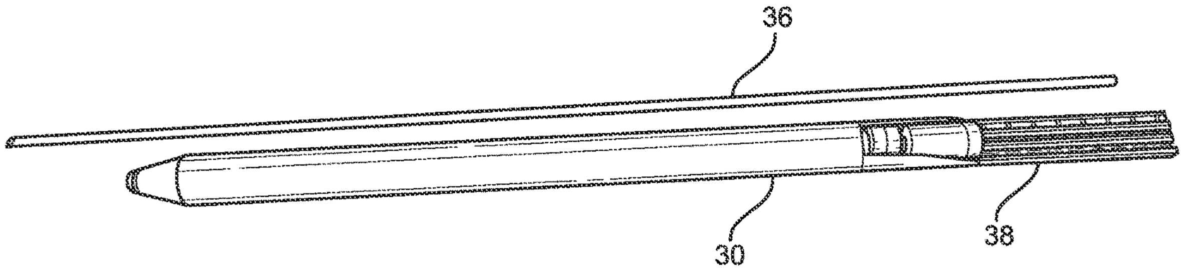
Figure 17B:
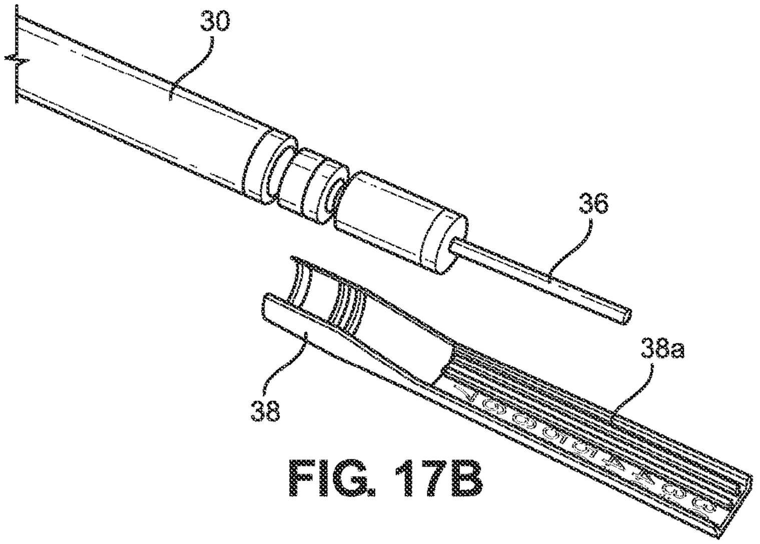
Figure 18A:
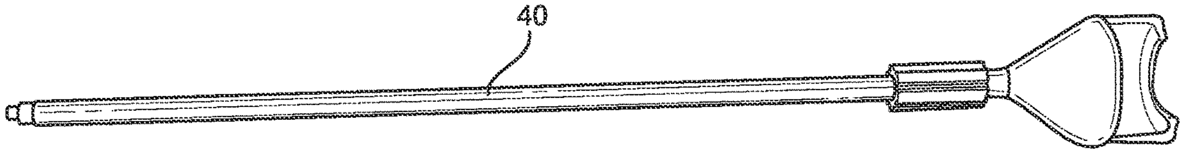
Figure 18B:
Figure 19:
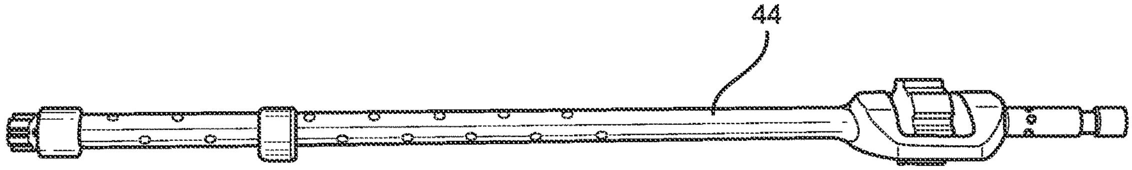

FIG. 16 shows a conventional pin holder 34. FIGS. 17A-17B show the first tissue dilator 30 with a pin 36 such as a Steinmann or exchange pin, and a specially configured depth gauge 38 having depth markings 38*a* thereon. FIG. 18A shows a funnel 40 and FIG. 18B shows a plunger 42 that is usable with the bone funnel 40. FIG. 19 shows a screw inserter 44 used for installation (and removal if necessary) of the bone screw 10.

FIGS. 20A-40B

FIGS. 20A-40B depict use of the fixation system by a physician and methodologies for installation of the bone screws 10 according to the disclosure. As depicted, the surgical procedure involves bone fixation of the sacroiliac (SI) joint. For such a procedure, the bones screws 10 utilized have diameters of Ø8 mm or Ø12 mm or Ø14 mm, it being appreciated that the system may be utilized with screws of other dimension. It will be appreciated that the described surgical procedure is provided for the purposes of an example of use of the fixation system and that the system may be utilized in a variety of surgical procedures in a variety of ways.

Figures 20A, 20B, 20C:
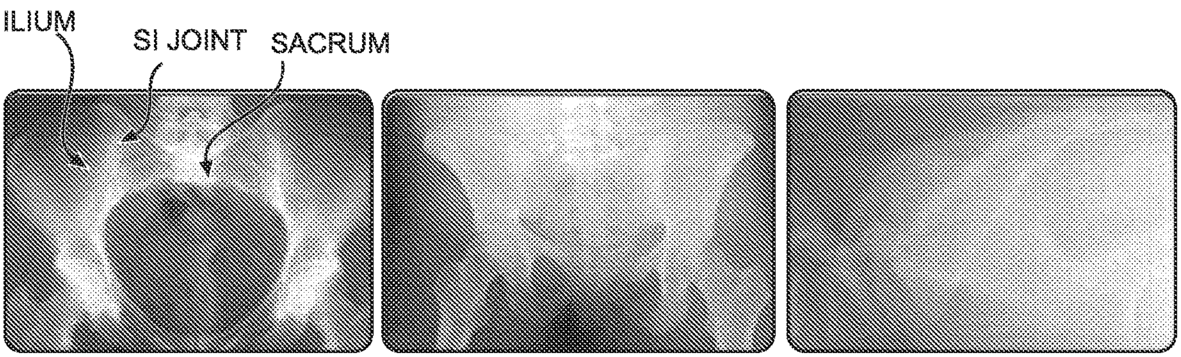

FIGS. 20A-20C depict pre-operative planning involving radiological imaging of the patient in the prone position, with 20A being an inlet view that allows the pelvic brim to be viewed, 20B being an outlet view that allows the sacral foramen to be viewed, and FIG. 20C being a lateral view that allows the alar lines, posterior/anterior sacral walls, and the 51 vertebrae endplate to be viewed. As seen, the lateral image is used to locate the superimposed alar slope, anterior sacral wall and posterior or linear sacral wall with the pin 36 and to mark the skin of the patient to create a triangular working area for positioning of the bone screw 10.

Figure 21:
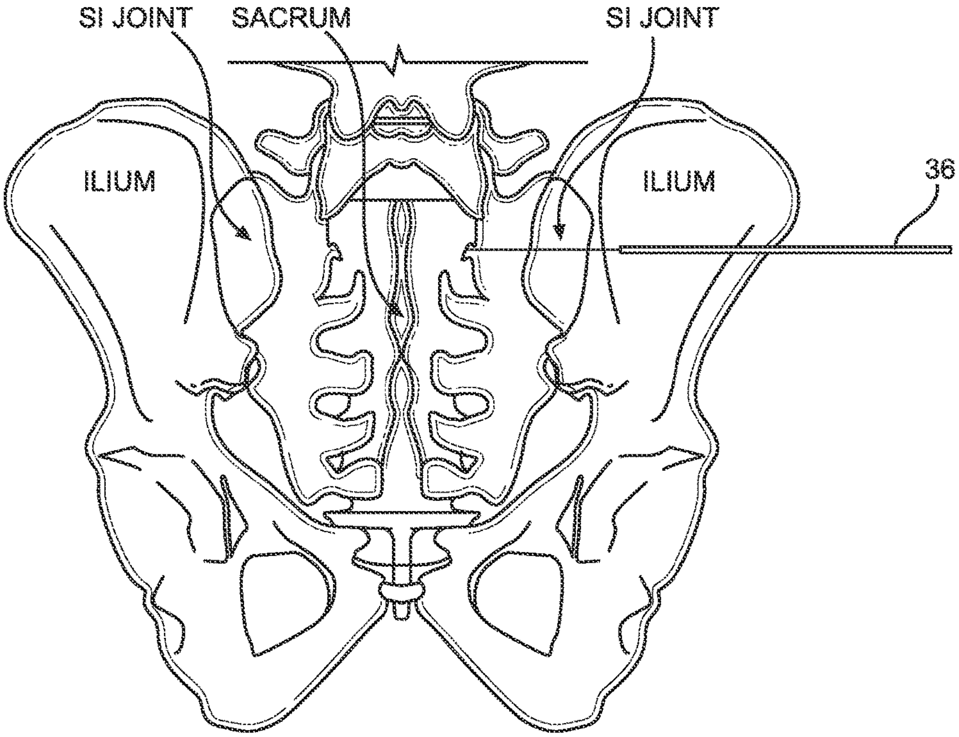

Next, as depicted in FIG. 21, the pin 36 is inserted across the SI joint spaced away from the alar line and slightly towards the anterior cortex. The pin 36 desirably points to just above the 51 nerve root foramen seen on the outlet view. The final position of the pin 36 is spaced slightly from the anterior sacral wall, avoiding the entrance to the pelvis, and just lateral of the posterior to the 51 neuroforamen.

Figure 22A:
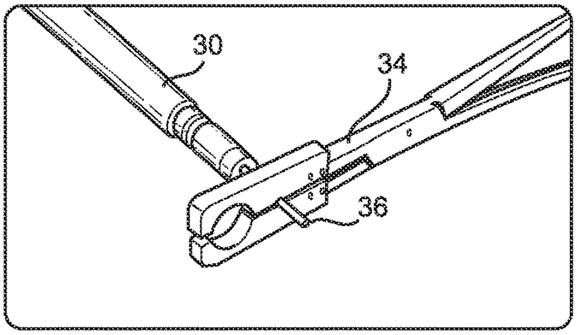
Figure 22B:
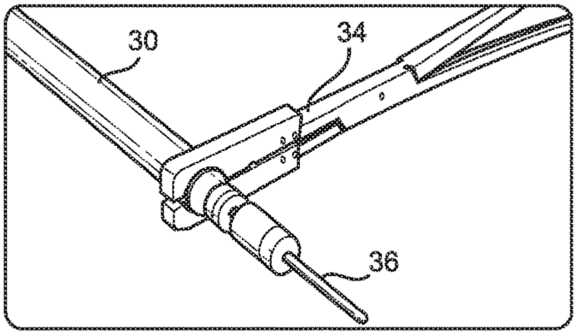

Using a mallet (such as the mallet 56 shown in FIG. 33) the physician impacts the pin 36 into the ilium and sacrum to a desired depth and at a desired trajectory. To add stability to the pin 36 during impaction of the pin 36, as depicted in FIGS. 22A and 22B, the first dilator 30 is desirably initially slid over the pin 36 or the pin holder 34 is used to stabilize the pin 36 or the first dilator 30 while targeting the intended screw position and trajectory.

Figure 23A:
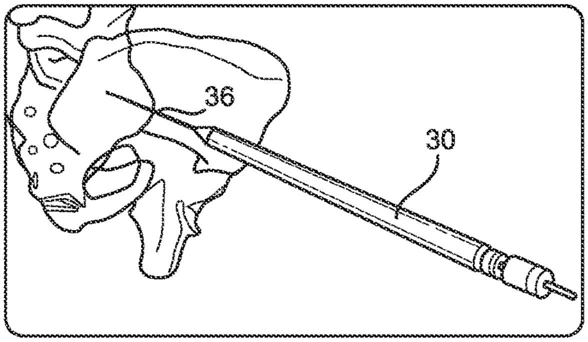
Figure 23B:
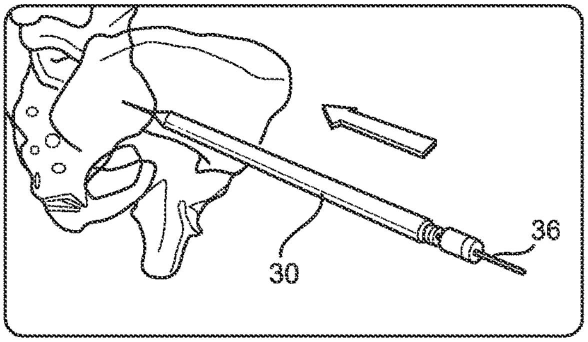
Figure 24A:
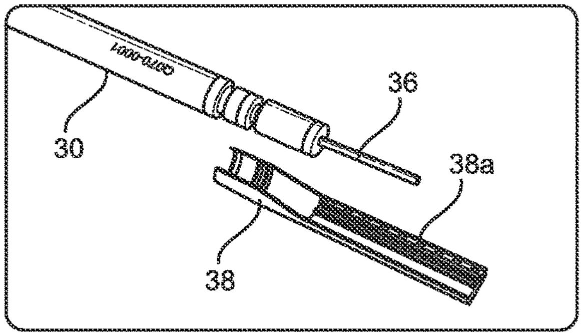
Figure 24B:
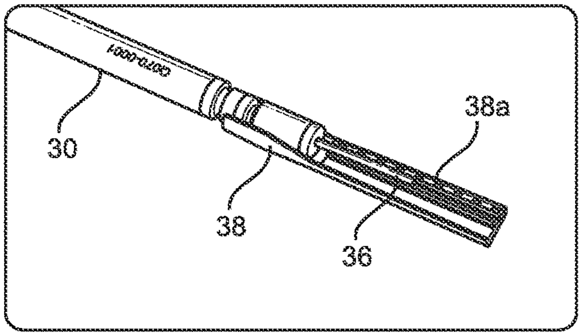

Next, as shown in FIGS. 23A-23B, the first dilator 30 is placed over the pin 36 until the distal end of the first dilator 30 is flush against the iliac cortex. Following this, as shown in FIGS. 24A-24B, the depth gauge 38 is snapped onto the proximal end of the first dilator 30. A bone screw 10 of appropriate length is selected by reading the depth marking 38*a* that aligns with the proximal end of the pin 36. In the event the pin 36 does not exactly align with one of the depth markings 38*a*, it is recommended to select one of the screws 10 having a length corresponding to the shorter marking 38*a*.

Figure 25:
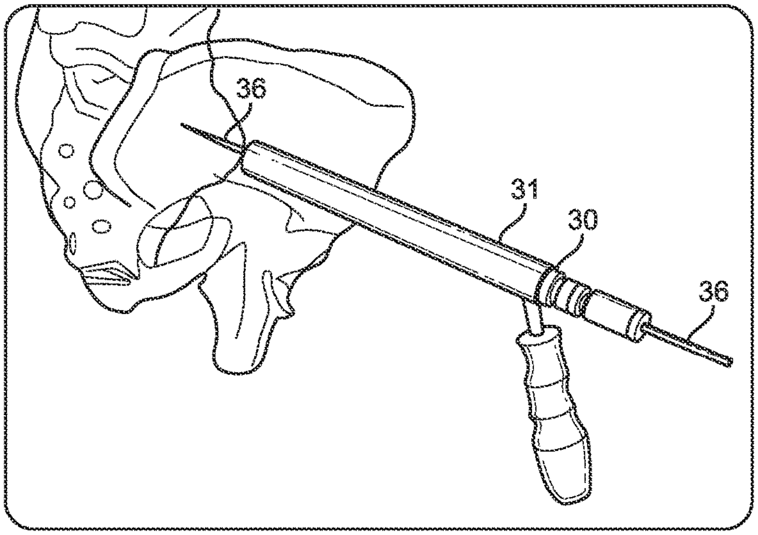
Figure 26A:
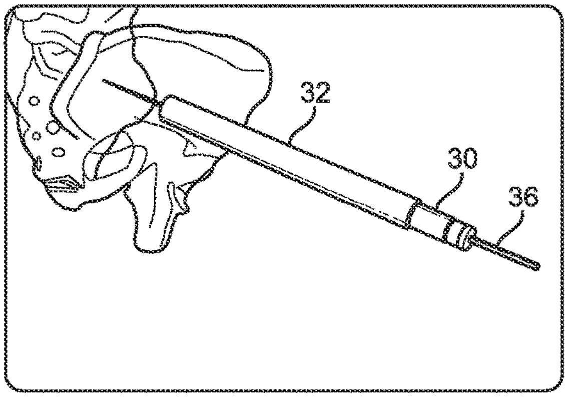
Figure 26B:
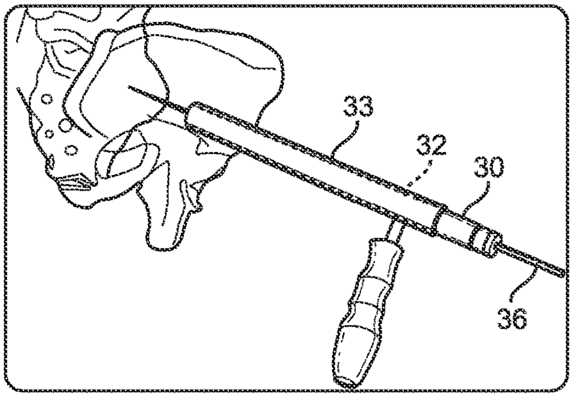

Next, with reference to FIG. 25, if the selected screw 10 to be inserted has a diameter of Ø8 mm or Ø12 mm, the second handled dilator 31 is slid over the first dilator 30 as the final dilator. However, with reference to FIGS. 26A-26B, if the selected screw 10 to be inserted has a diameter of Ø14 mm, the second dilator 32, which does not have a handle, is slid over the first dilator 30, and the third handled dilator 33 is slid over the second dilator 31 as the final dilator.

Figure 27:
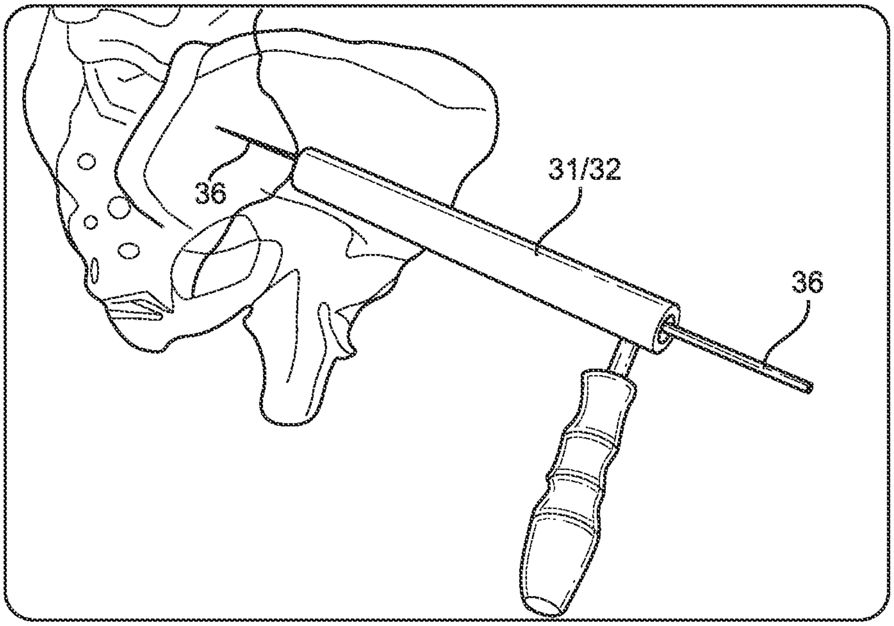
Figure 28:
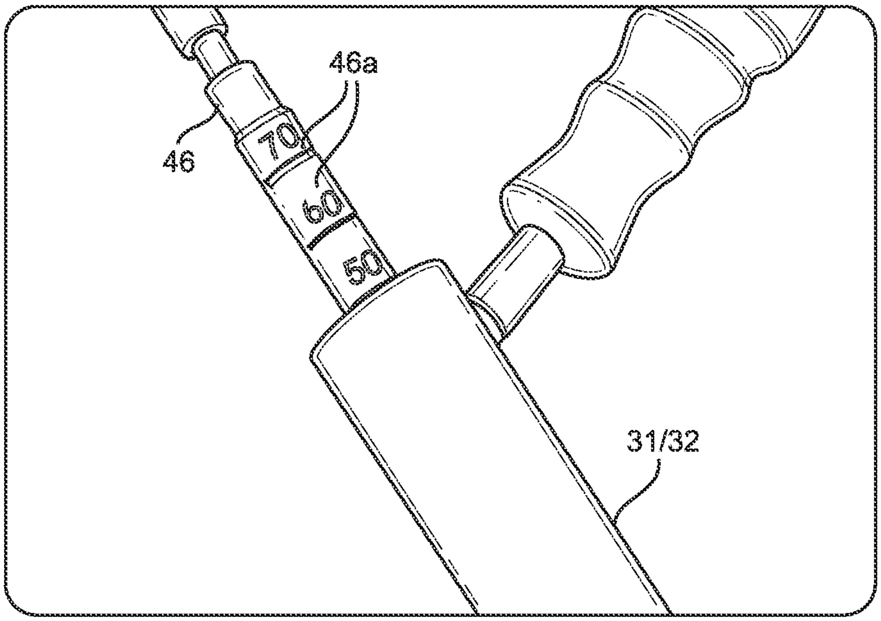

Next, as depicted in FIG. 27, the internal dilators (30 and 32) are removed and the final handled dilator (31 or 32) and the pin 36 remain in place. Thus, if the screw 10 to be inserted has a diameter of Ø8 mm or Ø12 mm, the final handled dilator in FIG. 27 will be the second handled dilator 31. If the screw to be inserted has a diameter of Ø14 mm, the final handled dilator in FIG. 27 will be the third handled dilator 33.

Following this, a hole into the bone is prepared for receiving the bone screw 10. With initial reference to FIG. 28, the hole into the bone may be accomplished using a cannulated drill or tap 46 having depth markings 46*a* received within the dilator 31/33. The drill or tap 46 is undersized to the corresponding screw diameter and the depth markings 46*a* indicate the prepared depth of the hole to be formed relative to the proximal end of the final and remaining dilator 31/33.

Figure 29:
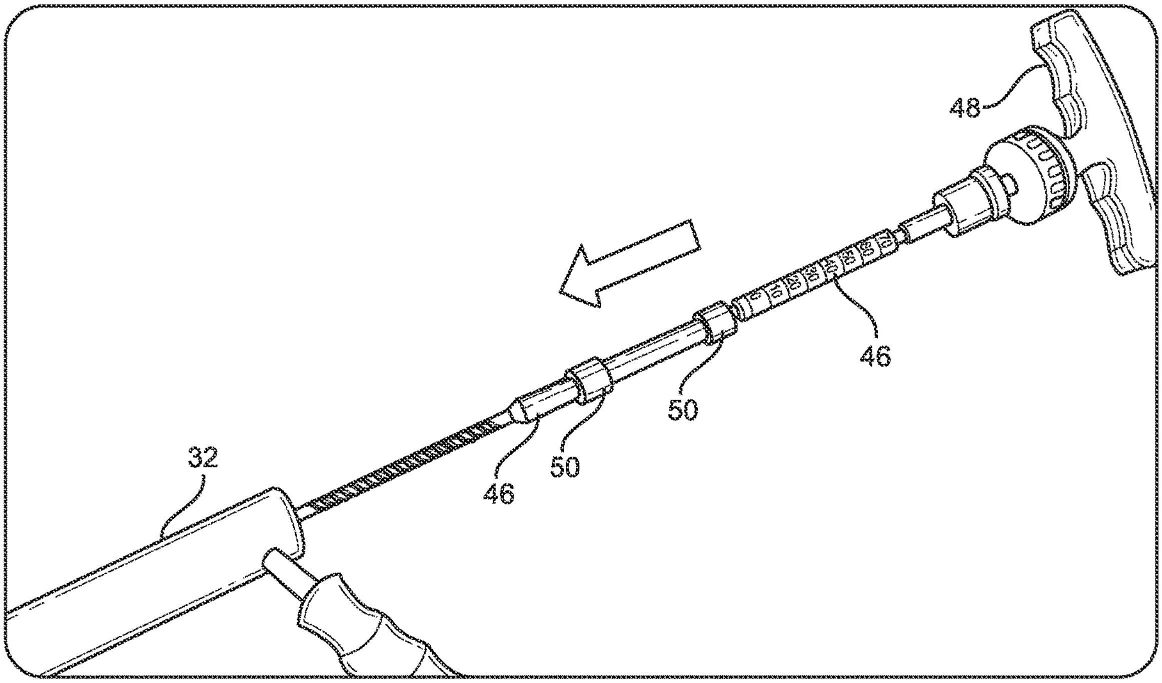
Figure 30A:
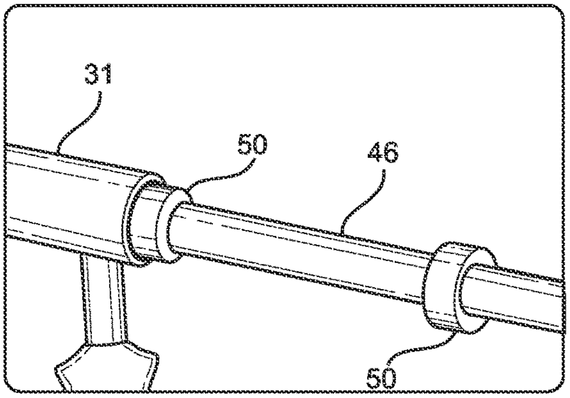
Figure 30B:
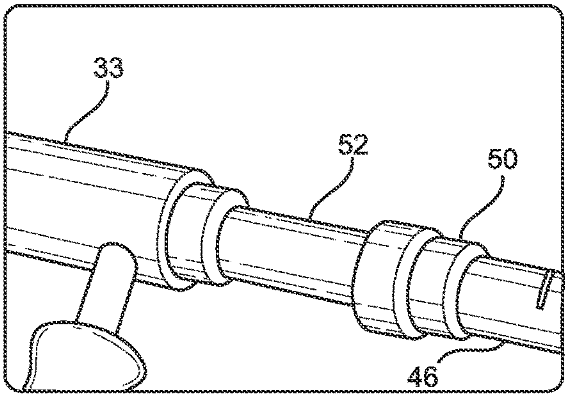

Next, as seen in FIG. 29, a cannulated ratcheting T-handle 48 or like unpowered or powered instrument is attached to the drill or tap 46 and is guided over the pin 36 and through the final dilator 31/33. As shown in FIG. 30A, if the final dilator is the second handled dilator 31, then collars 50 are utilized. If the final dilator is the larger third handled dilator 33, as shown in FIG. 30B, a dilator adapter 52 is included between the collars 50 for better alignment through the third handled dilator 33.

Figure 31:
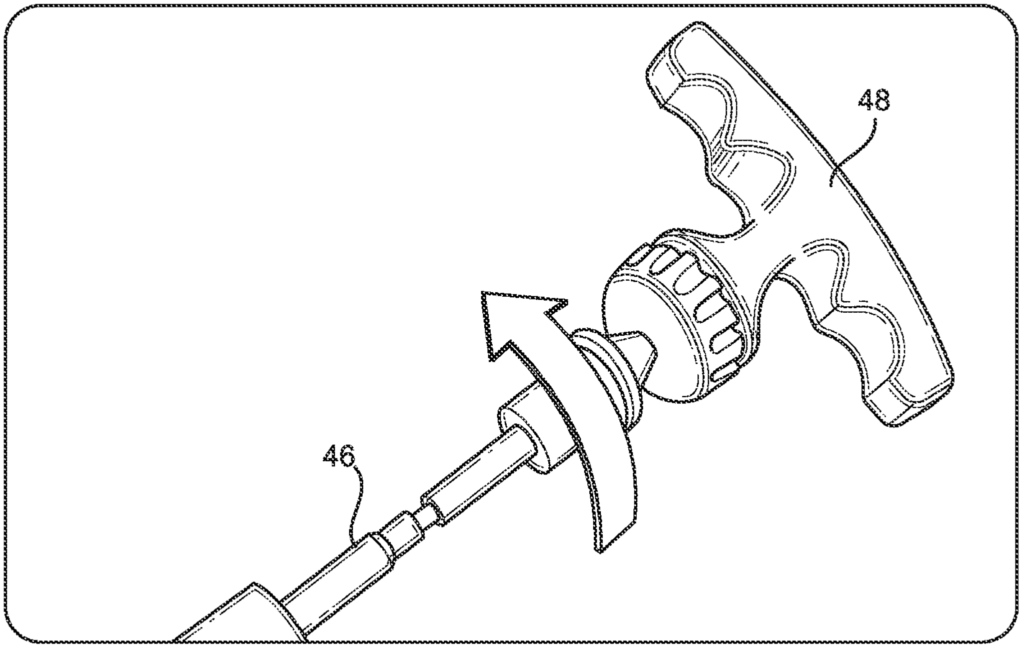
Figure 32:
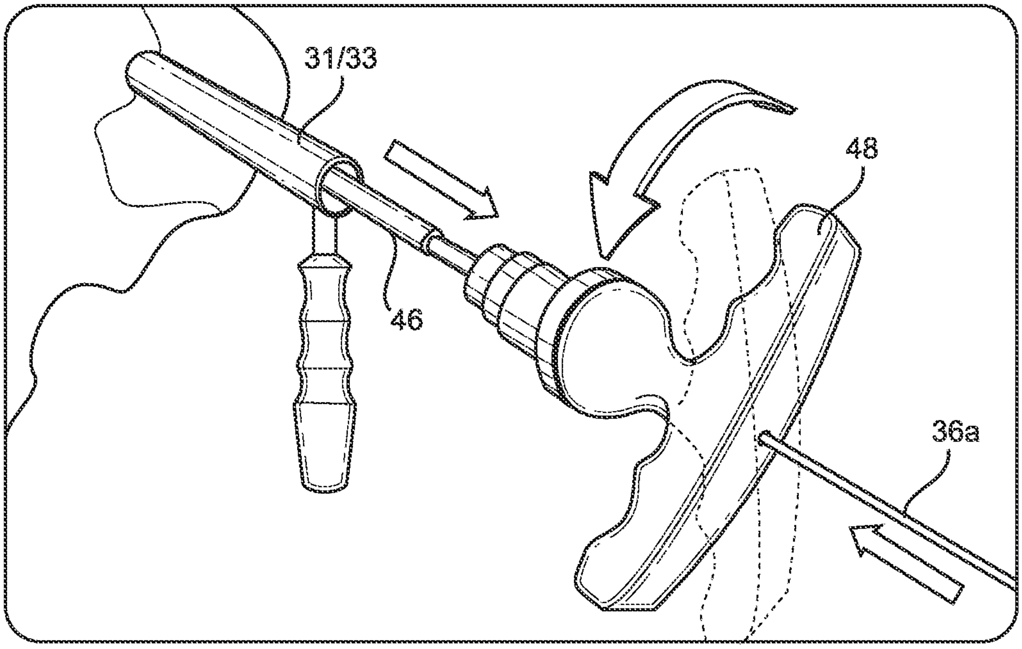

Next, as shown in FIG. 31, the ratcheting T-handle 48 is used to drive the drill or tap 46 into the bone to the desired depth. Following this, as depicted in FIG. 32, a counter-clockwise motion is used to remove the ratcheting T-handle 48. However, prior to guiding the ratcheting T-handle 48 and the drill or tap 46 off of the pin 36, an exchange pin 36*a* is inserted through the cannulation of the ratcheting T-handle 48 and the drill or tap 46 to abut the pin 36 and apply downward force to the pin 36. While downward force is maintained on the pin 36, the ratcheting T-handle 48 and the drill or tap 46 is guided off of the pin 36 and the ratcheting T-handle 48 and the drill or tap 46 and the exchange pin 36*a* are removed.

Figure 33:
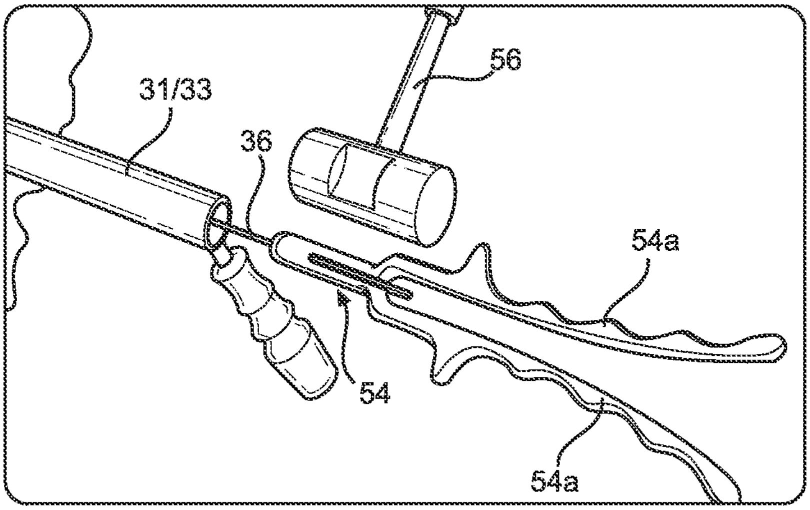

In the event the position of the pin 36 is deepened during the driving of the drill or tap 46, the position of the pin 36 may be adjusted as shown in FIG. 33. As shown, a pin puller 54 may be used by guiding the pin puller 54 over the pin 36, squeezing handles 54*a* of the pin puller 54 together and pulling proximally. A mallet 56 may be used to impact the pin puller 54 if additional force is needed to pull back the pin 36.

Once the hole in the bone is prepared, the bone screw 10 may be installed. FIGS. 34A-40B depict installation steps in accordance with the disclosure.

Figure 34A:
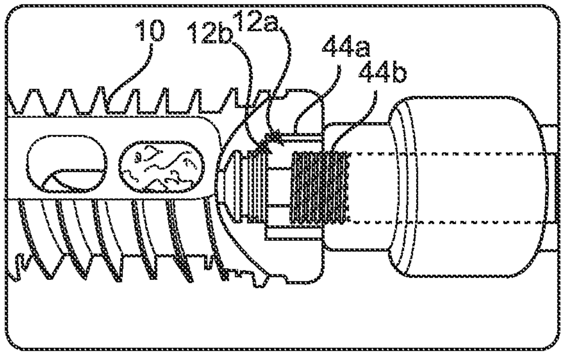
Figure 34B:
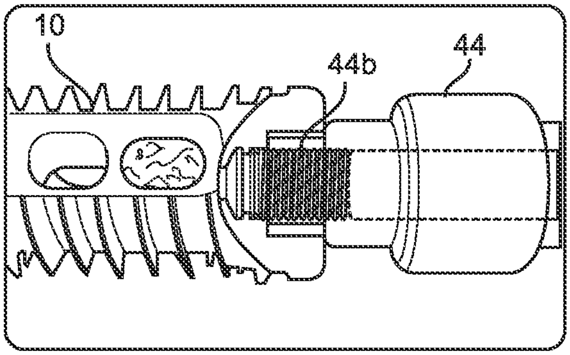

FIGS. 34A-34B show locating the screw inserter 44 onto the bone screw 10 by mating the hexalobe features and rotating the knob to thread into the internal threads 12*b* of the bone screw 10. In this regard, the screw inserter 44 corresponds to the screw inserter 12*c* described above and includes a hexalobe-shaped drive 44*a* that fits the drive 12*a* of the head 12 of the bone screw 10 and a threaded tip 44*b* that is threadable into the internal threads 12*b* of the head 12 of the bone screw 10.

Figure 35A:
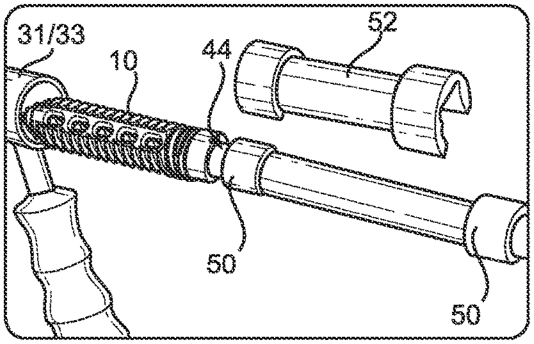
Figure 35B:
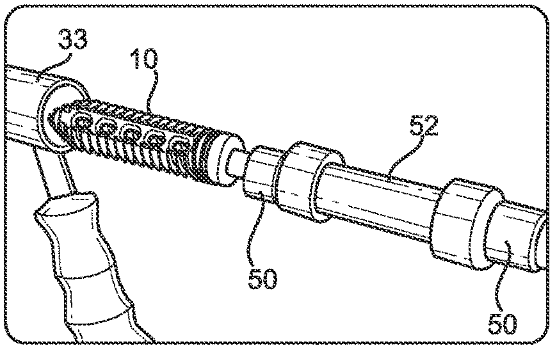

FIG. 35A depicts guiding of the bone screw 10 and the screw inserter 44 through the final dilator 31/33 and over the pin 36. In the event the final dilator is the larger third handled dilator 33, the third dilator adaptor 52 is preferably attached between the collar 50 for better alignment, as shown in FIG. 35B.

Figure 36A:
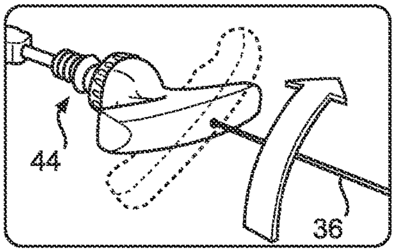
Figure 36B:
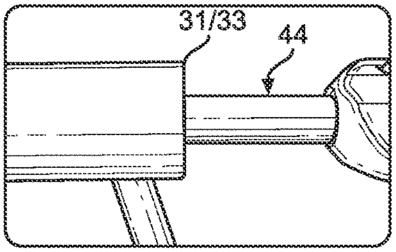
Figure 36C:
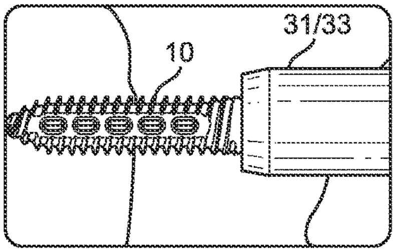
Figure 37A:
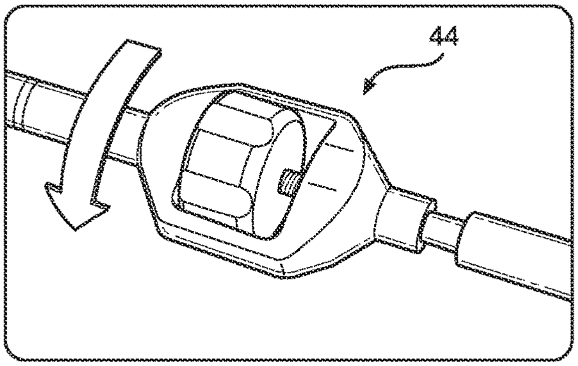
Figure 37B:
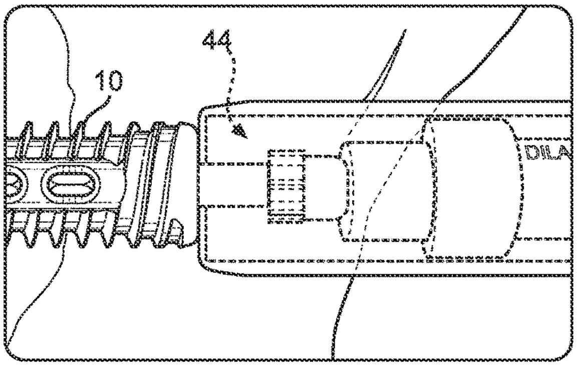

As depicted in FIGS. 36A-36C, the physician, using fluoroscopic guidance, will drive the bone screw 10 into the ilium towards the sacrum by rotating the screw inserter clockwise. Caution is taken not to advance the pin 36 during insertion of the bone screw 10 and confirmation is made that the bone screw 10 is seated to the desired depth and/or tightness. With reference to FIGS. 37A-37B, the screw inserter 44 is disengaged from the bone screw 10 by rotating the knob counterclockwise until disengaged. The screw inserter is then guided out of the final dilator 31/33 over the pin 36 to complete installation of the bone screw 10.

Figure 38:
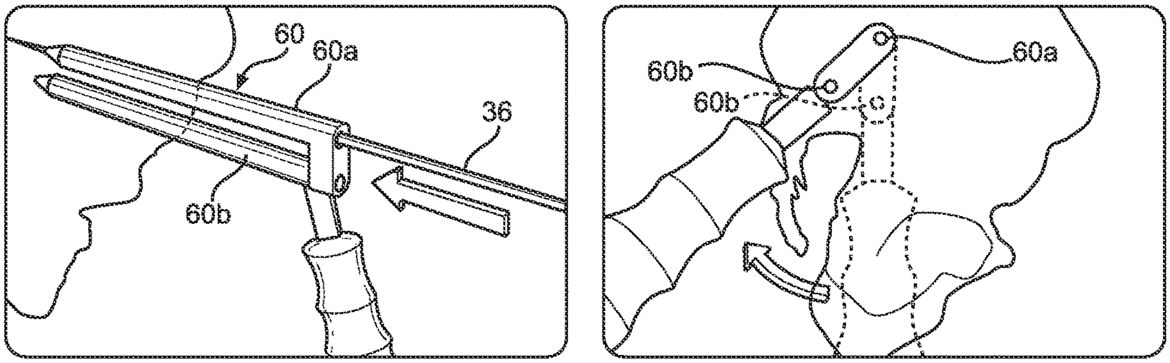

FIGS. 38A-40B depict steps in the event one or more additional bone screws 10 are to be installed in the fixation procedure. As shown in FIG. 38A, the final dilator 31/33 has been removed and a first tube 60*a* of a parallel pin guide 60 is slid over the pin 36. The pin guide 60 is rotated to position a second tube **60*b* adjacent the location that the next bone screw 10 is to be installed, as seen in FIG. 38**B.

Figures 39A, 39B, 39C:
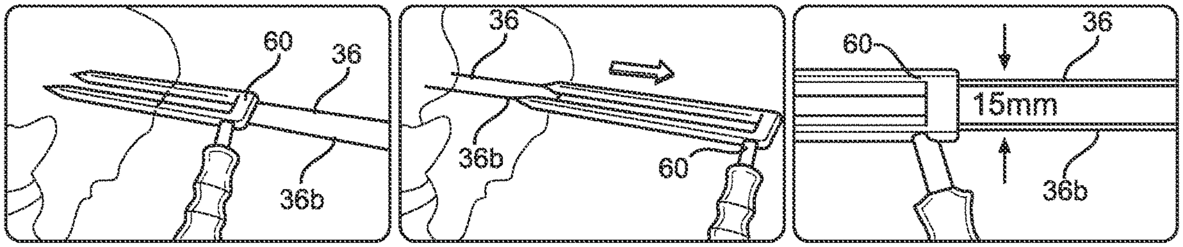

As depicted in FIGS. 39A-39C, a second pin **36*b* is impacted into the bone through the second tube 60*b*. Once the pin 36*b* is installed, the second bone screw 10 may be installed in the same manner as previously described for the first bone screw 10**.

Figures 40A, 40B:
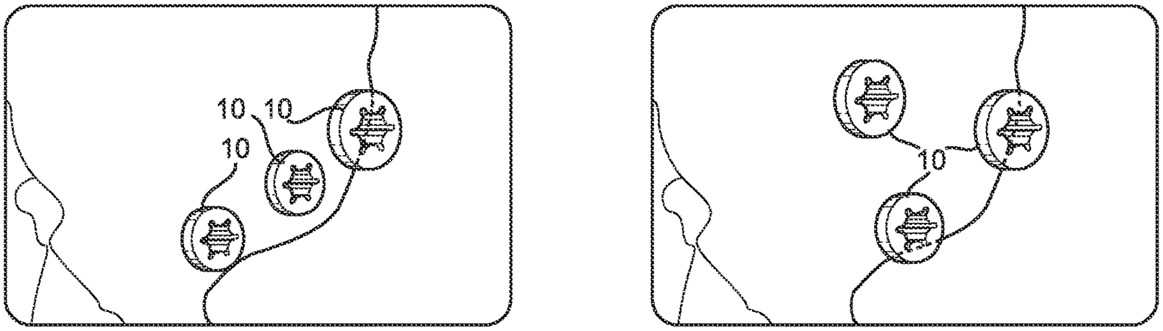
Figure 41A:
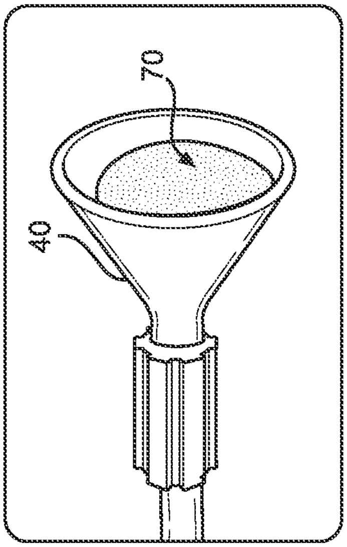
FIGS. 41A-42C depict packing of an installed bone screw with a bone graft material according to the disclosure.
Figure 41B:
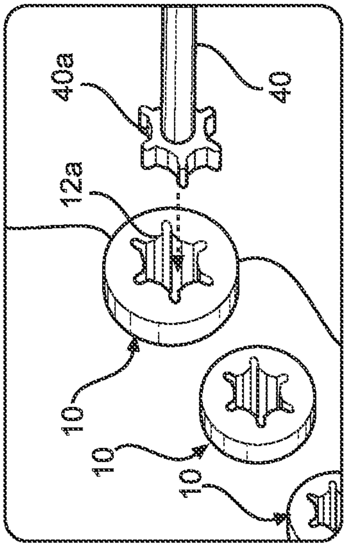
Figure 41C:
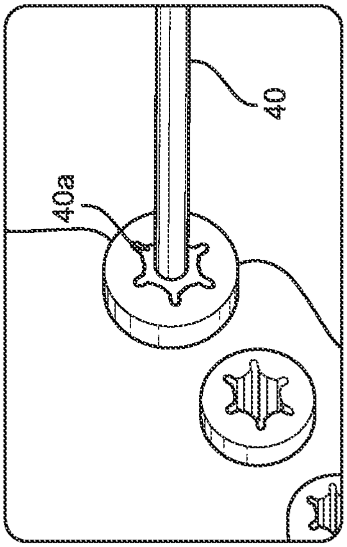
Figure 42A:
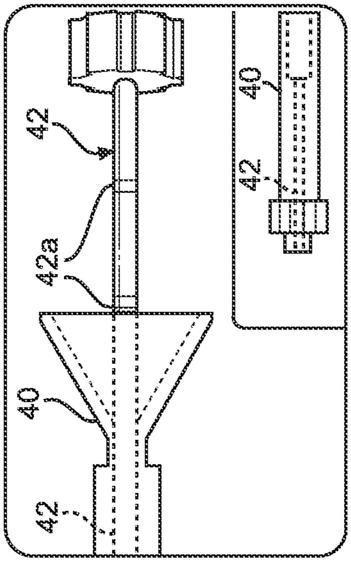
Figure 42B:
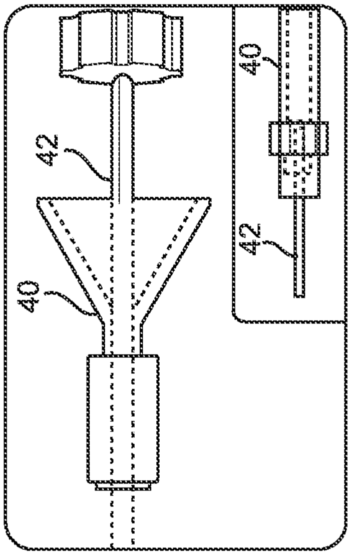
Figure 42C:
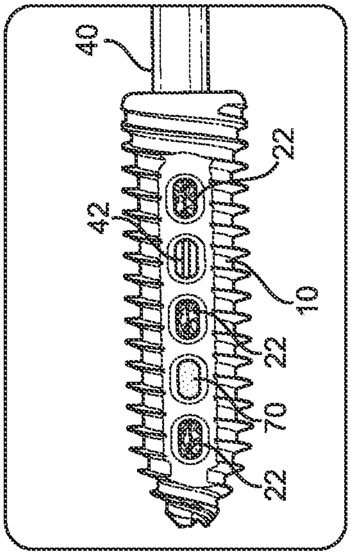

In the same manner, the parallel pin guide 60 may thereafter be used for installation of subsequent pins like the pins 36 and **36*b*, and additional ones of the bone screws 10 installed in like manner in desired locations. FIGS. 40A and 40B show two examples of three of the bone screws 10** installed for fixation of the SI joint.

FIGS. 41A-42C

FIGS. 41A-42C depict packing of an installed bone screw with a bone graft putty material 70 according to the disclosure. As shown, the funnel 40 is packed with the bone graft material 70. The pin 36 is removed and the hexalobe end **40*a* of the funnel 40 is mated with the drive 12*a* of the bone screw 10. The plunger 42 is pushed through the cannula of the funnel 40 to advance the bone graft material 70 to pack it into the bone screw 10. The plunger 42 includes depth markings 42*a*, such as 0 mm and 20 mm depth markings, to indicate plunger positioning past the distal tip of the funnel 40**.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A bone screw fixation system, comprising:

a pin configured to have a distal end installable into a bone;

a tissue dilator placeable over the pin with a distal end of the dilator proximate the distal end of the pin such that the pin extends past a proximal end of the tissue dilator; and a depth gauge having an inner surface with visual depth markings thereon, the depth gauge being removably positionable onto the proximal end of the dilator in a snap-fit relationship, wherein a proximal end of the pin substantially aligns with one of the depth markings to designate a length dimension; and a bone screw installable into the bone, the bone screw having a body having a screw head at one end of the screw, a screw tip at an opposite end of the screw, and a cannula extending from the screw head to the screw tip, wherein the bone screw has a length and the length of the bone screw is selected to correspond to the length dimension designated by the depth marking of the depth gauge that the proximal end of the pin is substantially aligned with.

2. A method for selecting a bone screw, comprising the steps of:

installing a distal end of a pin into a bone of a patient;

sliding a dilator over a proximal end of the pin;

providing a depth gauge having a plurality of visual depth markings along the surface of the depth gauge;

snap fitting the depth gauge onto a proximal end of the dilator so that the surface of the depth gauge faces and aligns with the pin and the visual depth markings are facing the pin; and selecting a bone screw of appropriate length by visually reading the visual depth markings and selecting one of the visual depth markings that aligns with a proximal end of the pin, or if one of the visual depth markings does not align with the proximal end of the pin, selecting one of the visual depth markings that is the closest visual depth marking short of the proximal end of the pin.

* * * * *